US006987121B2

(12) United States Patent  
Kliewer et al.

(10) Patent No.: US 6,987,121 B2  
(45) Date of Patent: Jan. 17, 2006

(54) COMPOSITIONS AND METHODS FOR HEPATOPROTECTION AND TREATMENT OF CHOLESTASIS

(75) Inventors: Steven Anthony Kliewer, Dallas, TX (US); Timothy Mark Willson, Durham, NC (US); Traci Mansfield, Guilford, CT (US)

(73) Assignee: SmithKline Beecham Corporation, Philadelphia, PA (US)

( * ) Notice: Subject to any disclaimer, the term of this patent is extended or adjusted under 35 U.S.C. 154(b) by 111 days.

(21) Appl. No.: 10/132,311

(22) Filed: Apr. 25, 2002

(65) Prior Publication Data

US 2003/0203939 A1 Oct. 30, 2003

(51) Int. Cl.  
*A61K 31/42* (2006.01)  
*A61K 31/44* (2006.01)

(52) U.S. Cl. .................. 514/378; 514/336; 514/340

(58) Field of Classification Search ................ 514/336, 514/340, 378, 326  
See application file for complete search history.

(56) References Cited

U.S. PATENT DOCUMENTS

| 6,187,814 B1 * | 2/2001 | Elias et al. ............. 514/531 |
| 2003/0130296 A1 | 7/2003 | Bauer et al. ............. 514/275 |

FOREIGN PATENT DOCUMENTS

| WO | WO 00/25134 | 5/2000 |
| WO | WO 00/37077 | 6/2000 |
| WO | WO 00/37077 A1 * | 6/2000 |
| WO | WO 00/57915 | 10/2000 |
| WO | WO 02/24632 | 3/2002 |
| WO | WO 02/020463 | 3/2002 |
| WO | WO 02/072598 | 9/2002 |
| WO | WO 03/015771 | 2/2003 |
| WO | WO 03/015777 | 2/2003 |
| WO | WO 03/016280 | 2/2003 |
| WO | WO 03/016288 | 2/2003 |
| WO | WO 03/042400 | 6/2003 |
| WO | WO 03/060078 | 7/2003 |

OTHER PUBLICATIONS

Willson, T. M. et al., Chemical Genomics: Functional Analysis of Orphan Nuclear Receptors in the Regulation of Bile Acid Metabolism, Medicinal Research Reviews, vol. 21, No. 6, 513–522, 2001.*

Willson T. M. et al., "Chemical genomics: Functional analysis of orphan nuclear recetprors in the regulation of bile acid metabolism", Abstract to Medicinal Research Reviews, 21(6), Nov. 2001, pp 513–522.*

Howard et al., "Catabolites of cholesterol synthesis pathways and forskolin as activators of the farnesoid X–activated nuclear receptor," *Toxicology and Applied Pharmacology* 163:195–202 (2000).

Beuers et al., "Ursodeoxycholic acid in cholestasis: potential mechanisms of action and therapeutic applications," *Hepatology* 28(6):1449–1453 (1998).

Goodwin et al., "A regulatory cascade of the nuclear receptors FXR, SJP–1, and LRH–1 represses bile acid biosynthesis," *Molecular Cell* 6:517–526 (Sep. 2000).

Greve et al., "Bile acids inhibit endotoxin–induced release of tumor necrosis factor by monocytes: An in vitro study," *Hepatology* 10(4):454–458 (1989).

Grober et al., "Identification of a bile acid–responsive element in the human ileal bile acid–binding protein gene," *The Journal of Biological Chemistry* 274(42):29749–29754 (Oct. 1999).

Hofmann, "The continuing importance of bile acids in liver and intestinal disease," *Arch Intern Med* 159:2647–2658 (Dec. 1999).

Karpen, "Bile acids go nuclear!," *Hepatology* 30(4):1107–1109 (Oct. 1999).

Kerr et al., "Loss of nuclear receptor SHP impairs but does not eliminate negative feedback regulation of bile acid synthesis," *Development Cell* 2:713–720 (Jun. 2002).

Kumar et al., "Use of ursodeoxycholic acid in liver diseases," *Journal of Gastroenterology and Hepatology* 16:3–14 (2001).

Leuschner et al., "Ursodeoxycholic acid in primary biliary cirrhosis: results of a controlled double–blind trial," *Gastroenterology* 97:1268–1274 (1989).

Lu et al., "Molecular basis for feedback regulation of bile acid synthesis by nuclear receptors," *Molecular Cell* 6:507–515 (2000).

Lu et al., "Orphan nuclear receptors as eLiXiRs and FiXeRs of sterol metabolism," *The Journal of Biological Chemistry* 276(41):37735–37738 (Oct. 2001).

Makishima et al., "Identification of a nuclear receptor for bile acids," *Science* 284:1362–1365 (May 1999).

Maloney et al., "Identification of a chemical tool for the orphan nuclear receptor FXR," *Journal of Medicinal Chemistry* 43(16):2971–2974 (Aug. 2000).

Parks et al., "Bile acids: natural ligands for an orphan nuclear receptor," *Science* 284:1365–1368 (May 1999).

Podda et al., "Ursodeoxycholic acid for chronic liver diseases," *J. Clin. Gastroenterol.* 10(Suppl 2):S25–S31 (1988).

Poupon et al., "Ursodeoxycholic acid therapy of chronic cholestatic conditions in aduls and children," *Pharmac. Ther.* 66:1–15 (1995).

Sinal et al., "Targeted disruption of the nuclear receptor FXR/BAR Impairs bile acid and lipid homeostasis," *Cell* 102:731–744 (Sep. 2000).

(Continued)

*Primary Examiner*—Dwayne Jones  
(74) *Attorney, Agent, or Firm*—Virginia G. Campen

(57) ABSTRACT

Methods for the treatment of cholestatic liver disease and reduction and prevention of hepatic injury resulting from cholestasis via administration of a FXR ligand are provided.

5 Claims, 1 Drawing Sheet

OTHER PUBLICATIONS

Wang et al., "Endogenous bile acids are ligands for the nuclear receptor FXR/BAR," *Molecular Cell* 3:543–553 (May 1999).

Willson et al., "Chemical genomics: functional analysis of orphan nuclear receptors in the regulation of bile acid metabolism," *Medicinal Research Reviews* 21(6):513–522 (2001).

Ananthanarayanan et al., "Human bile salt export pump promoter is transactivated by the farnesoid X receptor/bile acid receptor," *The Journal of Biological Chemistry* 276(31):28857–28865 (Aug. 2001).

Arrese et al., "New horizons in the regulation of bile acid and lipid homeostasis: critical role of the nuclear receptor FXR as an intracellular bile acid sensor," *GUT* 49:465–466 (2001).

Forman et al., "Identification of a nuclear receptor that is activated by farnesol metabolites," *Cell* 81:687–693 (Jun. 1995).

Goulis et al., "Randomised controlled trials of ursodeoxycholic–acid therapy for primary biliary cirrhosis: a meta–analysis," *The Lancet* 354:1053–1060 (Sep. 1999).

Fiorucci et al., "A novel and potent FXR agonist inhibits endogenous bile acids synthesis and protects against cholestasis," *Gastroenterology* 122(4)(Suppl 1):A–444 (Abstract T1262) (Apr. 2002) (Abstracts from the 103$^{rd}$ Annual Meeting of the American Gastroenterological Association, May 19–22, 2002, San Francisco, CA).

Suwannaroj et al., "Suppression of renal disease and mortality in the female NZBxNZW $F_1$ mouse model of systemic lupus erythematosus (SLE) by chenodeoxycholic acid," *Lupus* 10:562–567 (2001).

Denson et al., The Orphan Nuclear Receptor, shp, Mediates Bile Acid–Induced Inhibition of the Rat Bile Acid Transporter, ntcp, Gastroenterology 121:140–147 (2001).

* cited by examiner

COMPOSITIONS AND METHODS FOR HEPATOPROTECTION AND TREATMENT OF CHOLESTASIS

FIELD OF THE INVENTION

The present invention relates to the use of nuclear receptor ligands, and in particular ligands for Farnesoid X Receptor (FXR), as hepatoprotective agents against injury from cholestatic liver diseases and in the treatment of cholestasis.

BACKGROUND OF THE INVENTION

Cholestasis is defined as the impairment or cessation of bile flow and occurs in a variety of human liver diseases. Although there are various pathogenic causes of cholestasis, hepatocellular injury and associated liver dysfunction commonly result (Trauner et al. N. Engl. J. Med. 1998 339:1217–27). Ursodeoxycholic acid (UDCA) is currently the only established drug for the treatment of a variety of cholestatic liver diseases, such as primary biliary cirrhosis, primary sclerosing cholangitis, cystic fibrosis, and intrahepatic cholestasis of pregnancy (Kumar, D. and Tnadon, R. K. J. Gastroenterol. Hepatol. 2001 16:3–14; Beuers et al. Hepatology 1998 28:1449–53; Poupon, R. and Poupon, R. E. Pharmacol. Ther. 1995 66:1–15). The molecular mechanisms underlying the therapeutic benefits of UDCA are not fully understood but may be a result of immunomodulatory, antiapoptotic, cytoprotective and choleretic effects (Beuers et al. Hepatology 1998 28:1449–53).

Farnesoid X receptor (FXR) is a member of the nuclear receptor superfamily of ligand activated transcription factors (Lu et al. J. Biol. Chem. 2001 17:17). FXR is reported to bind and be activated by a variety of naturally occurring bile acids, including the primary bile acid chenodeoxycholic acid and its taurine and glycine conjugates (Makishima et al. Science 1999 284:1362–5; Parks et al. Science 1999 284:1365–8; and Wang et al. Mol. Cell. 1999 3:543–53). A number of recent studies have implicated FXR in the regulation of genes encoding proteins involved in the biosynthesis and transport of bile acids (Sinal et al. Cell 2000 102:731–44; Lu et al. Mol. Cell 2000 6:507–15; Goodwin et al. Mol. Cell. 2000 6:517–26; Grober et al. J. Biol. Chem. 1999 274:29749–54).

Using a potent selective FXR ligand, it has now been found that FXR ligands are hepatoprotective in bile duct-ligated (BDL) rats, a well-characterized model of extrahepatic cholestasis. These data are indicative of FXR ligands being effective in the treatment of cholestatic liver disease.

SUMMARY OF THE INVENTION

An object of the present invention is to provide a method to improve liver function in a patient with impaired bile flow which comprises administering to the patient a therapeutically effective amount of an FXR ligand.

Another object of the present invention is to provide a method for treating cholestatic liver disease which comprises administering to a patient in need of such treatment a therapeutically effective amount of a FXR ligand sufficient to improve serum markers of liver function.

Another object of the present invention is to provide a method for reducing or preventing development of cholestatic liver disease which comprises administering to a patient in need of such treatment an amount of a FXR ligand sufficient to effect the reduction or prevention of cholestatic liver disease.

DETAILED DESCRIPTION OF THE INVENTION

Figure 1:
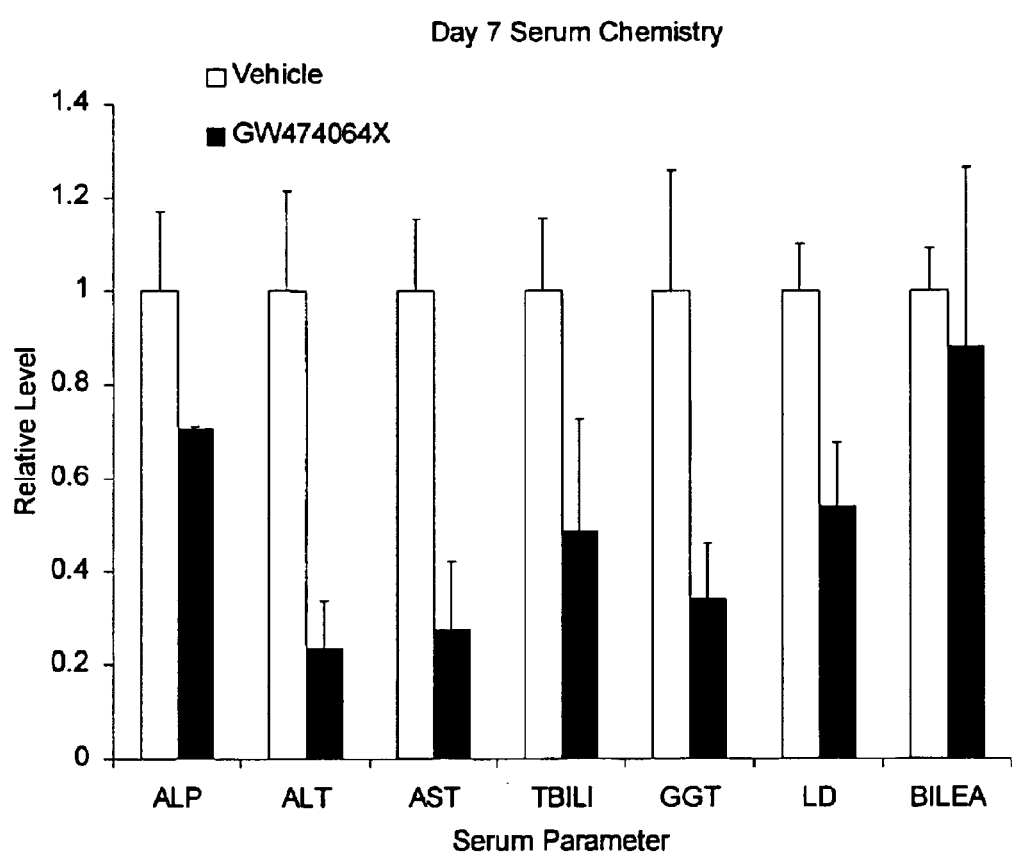
FIG. 1 shows the effect of treatment with an FXR ligand on markers of liver function in BDL rats. BDL ligated rats were treated with the FXR ligand GW4064 for 7 days as described in Example 1. Serum markers of liver function were determined. Data are mean±SEM from 6 rats and are expressed as a percentage of animals receiving vehicle alone.

Ligand binding of the FXR nuclear receptor can result in the alteration of expression of various genes that FXR aids in regulating, including genes involved in lipid absorption and digestion in the small intestine and lipid homeostasis in the liver. Examples of such genes include, but are not limited to, genes involved in bile acid transport, lipid absorption, cholesterol biosynthesis, proteolysis, amino acid metabolism, glucose biosynthesis, protein translation, electron transport, and hepatic fatty acid metabolism. FXR often functions as a heterodimer with the Retinoid X Receptor (the FXR/RXR heterodimer). The inventive method herein includes using this technology to affect bile acid and cholesterol homeostasis such that, ultimately, liver injury from cholestatic liver diseases is prevented or reduced and in treating cholestatic liver diseases in a mammal, including man. Thus the present invention provides methods for treating cholestatic liver diseases in a patient in need thereof via administration of an FXR ligand.

By "cholestatic liver disease" it is meant to be inclusive of any condition that impairs bile flow and results in impairment of liver function. Examples of such conditions include, but are not limited to cholestatic liver diseases, such as primary biliary cirrhosis, primary sclerosing cholangitis, cystic fibrosis, and intrahepatic cholestasis of pregnancy.

By "treating", as used herein, it is meant to affect the manifestations of the disease or condition in a manner beneficial to the health of the individual, such as to reduce symptoms or to slow, halt or reduce one or more molecular, macromolecular or cellular mechanisms of the disease. Treatment of cholestasis can therefore include stabilization or reduction of liver damage resulting directly or indirectly from cholestasis. Stabilization or reduction of liver damage can be measured, for example, by monitoring for reduction in levels of serum markers of liver damage. Examples of such serum markers include, but are not limited to, enzymes such as alanine aminotransferase (ALT), asparate aminotransferase (AST), and γ-glutamyl transferase (GGT). Accepted "normal" levels of these markers in human subjects are known in the medical art; "normal" may lie within a range of values, and the accepted "normal" range may vary depending on the condition of the subject (age, weight, concurrent medical conditions, medications, etc.), as will be apparent to one skilled in the art. Total bilirubin and bile acids can also be monitored to assess liver damage and reduction or stabilization thereof. By treating, for the purposes of the present invention, it is also meant to be inclusive of improvement in liver function, where liver function has been impaired due to decreased, impaired or ceased bile flow in an individual. A 'therapeutically effective amount' of an FXR ligand, in the treatment of cholestatic liver disease, indicates an amount of FXR ligand that results in improvement in liver function, which may be measured or ascertained using any suitable means as are known in the art. Such means include measuring serum markers of liver function, and/or improvement in other signs and symptoms of liver disease as manifested in the treated subject.

By "FXR ligand" it is meant an agent that binds to and modulates the expression and/or activity of FXR. By "modulate" it is meant an upregulation or downregulation, or alteration in timing of expression and/or activity of FXR or other means of modulating as known in the art. In a preferred embodiment of the present invention, the FXR ligands are activators or agonists of FXR, thereby upregulating expression and/or activity of FXR.

The ability of an FXR ligand to decrease liver damage associated with cholestasis was demonstrated. In these experiments, bile duct-ligated (BDL) rats, a well-characterized model of extrahepatic cholestasis, were used to demonstrate FXR-dependent hepatoprotection. As shown in Table 1, below, ligation of the common bile duct in Sprague-Dawley rats resulted in a marked increase in serum markers of liver damage as compared to normal rats. Specifically, levels of alanine aminotransferase (ALT) were increased 3-fold as compared to normal rats, levels of asparate aminotransferase (AST) were increased 9-fold as compared to normal rats, and levels of γ-glutamyl transferase (GGT) were increased 48-fold as compared to normal rats. Serum levels of total bilirubin (TBILI) were also increased 172-fold as compared to normal rats and serum bile acids (BILEA) were increased 15.6-fold as compared to normal rats.

TABLE 1

Serum parameters for Normal and BDL Sprague-Dawley rats.

| Serum Parameter (Units) | Normal Rats[§] | BDL Rats[*] |
|---|---|---|
| ALT (U/L) | 64 ± 2 (46–85) | 217 ± 46 (127–337) |
| AST (U/L) | 111 ± 3 (81–162) | 1017 ± 156 (741–1598) |
| TBILI (mg/dL) | 0.058 ± 0.03 (0.01–0.094) | 10 ± 2 (7–14) |
| GGT (U/L) | 0.90 ± 0.08 (0.00–2.14) | 43 ± 11 (12–69) |
| BILEA (μmol/L) | 47.4 ± 3.36 (19–107) | 741 ± 68 (516–932) |

In Table 1, values for normal rats provided include the mean±standard error of the mean (SEM) followed by the range in parenthesis for a total of 43 animals. Values for BDL rats provided also include the mean±SEM followed by the range in parenthesis for a total of 6 animals.

The effects of the selective FXR ligand GW4064 on these markers of liver injury/function in BDL rats were then examined. GW4064 is a compound of Formula (I):

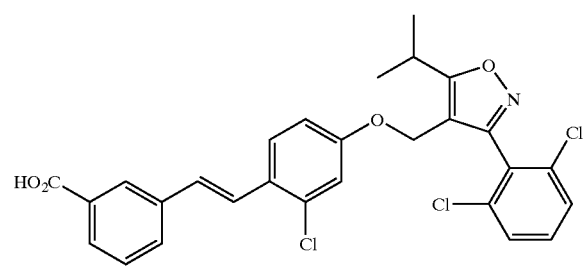

BDL rats were dosed daily with GW4064 or vehicle alone as described in the example. As shown in FIG. 1, BDL rats that received the FXR ligand GW4064 exhibited a pronounced improvement in liver function as defined by the panel of enzymes examined in this study. Serum levels of ALT, AST, TBILI, and GGT were reduced to 23%, 27%, 49%, and 34% of that in BDL rats receiving vehicle alone.

Thus, as shown by these experiments, activation of FXR results in a significant improvement in serum markers of liver injury in a surgical model of extrahepatic cholestasis.

Histological examinations were also performed on liver samples obtained from these animals. Slides from liver samples of vehicle-treated BDL rats showed large areas of necrosis as well as bile-duct proliferation. In contrast, slides from BDL rats treated with the FXR ligand GW4064 showed no necrosis, only bile duct proliferation. Slides of samples from sham ligated rats showed normal hepatocytes and normal liver histology.

Accordingly, data from these experiments are indicative of FXR ligands having therapeutic utility in the treatment of injury or impairment due to cholestasis.

Additional FXR ligands useful in the present inventions can be identified routinely by those of skill in the art based upon assays described in PCT/US99/30947, the teachings of which are herein incorporated by reference in their entirety. In a preferred embodiment, FXR ligands are identified using a nuclear receptor-peptide assay for identifying ligands. This assay utilizes fluorescence resonance energy transfer (FRET) and can be used to test whether putative ligands bind to FXR. The FRET assay is based upon the principle that ligands induce conformational changes in nuclear receptors that facilitate interactions with coactivator proteins required for transcriptional activation. In FRET, a fluorescent donor molecule transfers energy via a non-radioactive dipole-dipole interaction to an acceptor molecule (which is usually a fluorescent molecule). FRET is a standard spectroscopic technique for measuring distances in the 10–70 Å range. Upon energy transfer, which depends on the $R^{-6}$ distance between the donor and acceptor, the donor's fluorescence is reduced, and the acceptor fluorescence is increased, or sensitized. FRET is frequently used in both polymer science and structural biology and has recently been used to study macromolecular complexes of DNA, RNA, and proteins. In addition, Mathis has used europium cryptates with the multichromophoric Allophycocanin to achieve an extremely large $R_0$ of 90 Å (Mathis et al. Clin. Chem. 1993 39:1953–1959).

In addition to GW4064, a number of other FXR ligands useful in the methods of the present invention have been identified. For example, using the FRET assay it was demonstrated that chendeoxycholic acid (CDCA) binds and activates FXR. Additional FXR ligands identified by FRET and useful in the methods of the present invention are compounds of formula (II)

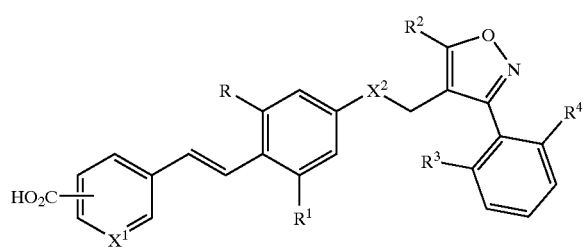

wherein $X^1$ is CH or N; $X^2$ is O or NH; R and $R^1$ are independently H, lower alkyl, halogen, or $CF_3$; $R^2$ is lower alkyl; $R^3$ and $R^4$ are independently H, lower alkyl, halogen, $CF_3$, OH, O-alkyl, or O-polyhaloalkyl.

The compounds of Formula (I) or (II) can be synthesized using standard techniques of organic chemistry. A convergent strategy can be employed in which a hydroxystilbene and a hydroxymethyisoxazole are prepared independently and then condensed using a Mitsunobu coupling to generate the ether linkage. Compounds with anilino linkages can be prepared by converting the hydroxyl residue of a hydroxymethyisoxazole into a leaving group, such as bromide or mesylate, followed by reaction with an aminostilbenes.

Hydroxymethylsoxazoles can be prepared by the condensation of a beta-keto ester enolate with an α-halo-substituted hydroxamic acid. The resulting esters can be reduced to an alcohol with a metal hydride reducting agent such as diisobutyl aluminum hydride (DIBAL).

Hydroxystilbenes can be prepared by Homer-Wadsworth-Emmons coupling of an aryl aldehyde and an arylmethylene phosphonate ester, or by Heck coupling of a styrene with an arylbromide, iodide, or triflate in the presence of a palladium catalyst. Using standard chemical methods, tritium or iodine 125 can be incorporated into the compounds of formula (I) and (II).

In a preferred embodiment, formula I, GW4064, is synthesized in accordance with procedures described by Maloney et al. J. Med. Chem. 43:2971–4.

FXR ligands used in the methods of the present invention are conveniently administered in the form of pharmaceutical compositions. Such pharmaceutical compositions comprising a FXR ligand may conveniently be presented for use in a conventional manner in admixture with one or more physiologically acceptable carriers or excipients.

FXR ligands useful in the methods of the present invention may be formulated for administration in any suitable manner. They may, for example, be formulated for topical administration or administration by inhalation or, more preferably, for oral, transdermal or parenteral administration. The pharmaceutical composition may be in a form such that it can effect controlled release of the FXR ligand. A particularly preferred method of administration, and corresponding formulation, is oral administration.

For oral administration, the pharmaceutical composition may take the form of, and be administered as, for example, tablets (including sub-lingual tablets) and capsules (each including timed release and sustained release formulations), pills, powders, granules, elixirs, tinctures, emulsions, solutions, syrups or suspensions prepared by conventional means with acceptable excipients.

For instance, for oral administration in the form of a tablet or capsule, the active FXR ligand can be combined with an oral, non-toxic pharmaceutically acceptable inert carrier such as ethanol, glycerol, water and the like. Powders are prepared by comminuting the compound to a suitable fine size and mixing with a similarly comminuted pharmaceutical carrier such as an edible carbohydrate, as, for example, starch or mannitol. Flavoring, preservative, dispersing and coloring agents can also be present.

Capsules can be made by preparing a powder mixture as described above, and filling formed gelatin sheaths. Glidants and lubricants such as colloidal silica, talc, magnesium stearate, calcium stearate or solid polyethylene glycol can be added to the powder mixture before the filling operation. A disintegrating or solubilizing agent such as agar-agar, calcium carbonate or sodium carbonate can also be added to improve the availability of the medicament when the capsule is ingested.

Moreover, when desired or necessary, suitable binders, lubricants, disintegrating agents and coloring agents can also be incorporated into the mixture. Suitable binders include starch, gelatin, natural sugars such as glucose or beta-lactose, corn sweeteners, natural and synthetic gums such as acacia, tragacanth or sodium alginate, carboxymethylcellulose, polyethylene glycol, waxes and the like. Lubricants used in these dosage forms include sodium oleate, sodium stearate, magnesium stearate, sodium benzoate, sodium acetate, sodium chloride and the like. Disintegrators include, without limitation, starch, methyl cellulose, agar, bentonite, xanthan gum and the like. Tablets are formulated, for example, by preparing a powder mixture, granulating or slugging, adding a lubricant and disintegrant and pressing into tablets. A powder mixture is prepared by mixing the compound, suitably comminuted, with a diluent or base as described above, and optionally, with a binder such as carboxymethylcellulose, an aliginate, gelatin, or polyvinyl pyrrolidone, a solution retardant such as paraffin, a resorption accelerator such as a quaternary salt and/or an absorption agent such as bentonite, kaolin or dicalcium phosphate. The powder mixture can be granulated by wetting with a binder such as syrup, starch paste, acadia mucilage or solutions of cellulosic or polymeric materials and forcing through a screen. As an alternative to granulating, the powder mixture can be run through the tablet machine and the result is imperfectly formed slugs broken into granules. The granules can be lubricated to prevent sticking to the tablet forming dies by means of the addition of stearic acid, a stearate salt, talc or mineral oil. The lubricated mixture is then compressed into tablets. FXR ligands useful in the methods of the present invention can also be combined with a free flowing inert carrier and compressed into tablets directly without going through the granulating or slugging steps. A clear or opaque protective coating consisting of a sealing coat of shellac, a coating of sugar or polymeric material and a polish coating of wax can be provided. Dyestuffs can be added to these coatings to distinguish different unit dosages.

Oral fluids such as solution, syrups and elixirs can be prepared in dosage unit form so that a given quantity contains a predetermined amount of the compound. Syrups can be prepared by dissolving the compound in a suitably flavored aqueous solution, while elixirs are prepared through the use of a non-toxic alcoholic vehicle. Suspensions can be formulated by dispersing the compound in a non-toxic vehicle. Solubilizers and emulsifiers such as ethoxylated isostearyl alcohols and polyoxy ethylene sorbitol ethers, preservatives, flavor additive such as peppermint oil or saccharin, and the like can also be added.

Where appropriate, dosage unit formulations for oral administration can be microencapsulated. The formulation can also be prepared to prolong or sustain the release as for example by coating or embedding particulate material in polymers, wax or the like.

FXR ligands for use in the methods of the present invention can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

FXR ligands for use in the methods of the present invention can also be administered in the form of liposome emulsion delivery systems, such as small unilamellar vesicles, large unilamellar vesicles and multilamellar vesicles. Liposomes can be formed from a variety of phospholipids, such as cholesterol, stearylamine or phosphatidylcholines.

FXR ligands for use in the methods of the present invention may also be delivered by the use of monoclonal antibodies as individual carriers to which the FXR ligand is coupled. FXR ligands for use in the methods of the present invention may also be coupled with soluble polymers as targetable drug carriers. Such polymers can include polyvinylpyrrolidone, pyran copolymer, polyhydroxypropylmethacrylamide-phenol, polyhydroxyethylaspartamidephenol, or polyethyleneoxide-polylysine substituted with palmitoyl residues. Furthermore, the compounds of the present invention may be coupled to a class of biodegradable polymers useful in achieving controlled release of a drug, for example, polylactic acid, polyepsilon caprolactone, polyhydroxy butyric acid, polyorthoesters, polyacetals, polydihydropyrans, polycyanoacrylates and cross-linked or amphipathic block copolymers of hydrogels.

The present invention includes pharmaceutical compositions containing 0.1 to 99.5%, more particularly, 0.5 to 90% of an FXR ligand in combination with a pharmaceutically acceptable carrier.

Compositions comprising a FXR ligand may also be administered in nasal, ophthalmic, otic, rectal, topical, intravenous (both bolus and infusion), intraperitoneal, intraarticular, subcutaneous or intramuscular inhalation or insufflation form, all using forms well known to those of ordinary skill in the pharmaceutical arts.

For transdermal administration, the pharmaceutical composition comprising the FXR ligand may be given in the form of a transdermal patch, such as a transdermal iontophoretic patch.

For parenteral administration, the pharmaceutical composition comprising the FXR ligand may be given as an injection or a continuous infusion (e.g. intravenously, intravascularly or subcutaneously). The compositions may take such forms as suspensions, solutions or emulsions in oily or aqueous vehicles and may contain formulatory agents such as suspending, stabilizing and/or dispersing agents. For administration by injection these may take the form of a unit dose presentation or as a multidose presentation preferably with an added preservative. Alternatively for parenteral administration the active ingredient may be in powder form for reconstitution with a suitable vehicle.

FXR ligands for use in the methods of the present invention may also be formulated as a depot preparation. Such long acting formulations may be administered by implantation (for example subcutaneously or intramuscularly) or by intramuscular injection. Thus, for example, the FXR ligand may be formulated with suitable polymeric or hydrophobic materials (for example as an emulsion in an acceptable oil) or ion exchange resins, or as sparingly soluble derivatives, for example, as a sparingly soluble salt.

Alternatively the FXR ligand may be formulated for topical application, for example in the form of ointments, creams, lotions, eye ointments, eye drops, ear drops, mouthwash, impregnated dressings and sutures and aerosols, and may contain appropriate conventional additives, including, for example, preservatives, solvents to assist drug penetration, and emollients in ointments and creams. Such topical formulations may also contain compatible conventional carriers, for example cream or ointment bases, and ethanol or oleyl alcohol for lotions. Such carriers may constitute from about 1% to about 98% by weight of the formulation; more usually they will constitute up to about 80% by weight of the formulation.

For administration by inhalation the FXR ligands are conveniently delivered in the form of an aerosol spray presentation from pressurized packs or a nebulizer, with the use of a suitable propellant, e.g. dichlorodifluoromethane, trichlorofluoromethane, dichlorotetrafluoroethane, tetrafluoroethane, heptafluoropropane, carbon dioxide or other suitable gas. In the case of a pressurized aerosol, the dosage unit may be determined by providing a valve to deliver a metered amount. Capsules and cartridges of, for example, gelatin, for use in an inhaler or insufflator may be formulated containing a powder mix of an FXR ligand and a suitable powder base such as lactose or starch.

Pharmaceutical compositions comprising a FXR ligand are administered in an amount effective for treatment or prophylaxis of cholestatic liver diseases and injury to the liver resulting from such diseases. Initial dosing in human is accompanied by clinical monitoring of symptoms for such conditions. In general, the compositions are administered in an amount of active agent of at least about 100 $\mu$g/kg body weight. In most cases they will be administered in one or more doses in an amount not in excess of about 20 mg/kg body weight per day. Preferably, in most cases, dose is from about 100 $\mu$g/kg to about 5 mg/kg body weight, daily. For administration particularly to mammals, and particularly humans, it is expected that the daily dosage level of the active agent will be from 0.1 mg/kg to 10 mg/kg and typically around 1 mg/kg. It will be appreciated that optimum dosage will be determined by standard methods for each treatment modality and indication, taking into account the indication, its severity, route of administration, complicating conditions and the like. The physician in any event will determine the actual dosage that will be most suitable for an individual and will vary with the age, weight and response of the particular individual. The effectiveness of a selected actual dose can readily be determined, for example, by measuring clinical symptoms or standard indicia of liver injury after administration of the selected dose. The above dosages are exemplary of the average case. There can, of course, be individual instances where higher or lower dosage ranges are merited, and such are within the scope of this invention. For conditions or disease states as are treated by the present invention, maintaining consistent daily levels in a subject over an extended period of time, e.g., in a maintenance regime, can be particularly beneficial.

The following nonlimiting example is provided to further illustrate the present invention.

EXAMPLE

Male Sprague-Dawley rats (approximately 300 grams) were obtained from Charles River Laboratories Inc (Raleigh, N.C.) and were maintained on a 12 hour light/12 hour dark light cycle. Animals were anesthetized by the administration of 2–3% isoflurane. Laparotomy was performed under sterile technique and the liver and duodenum gently displaced to reveal the common bile duct. The bile duct was separated from the surrounding tissue and two ligatures of 4-0 Ethilon were placed around it. The bile duct was clamped between the two ligatures with an aneurysm clamp and the ligatures drawn tight. An additional ligature was placed proximal to the first (near the liver). The clamp was removed and the bile duct severed between the ligatures. The muscle wall was closed with 4-0 Vicryl and the skin closed with staples. Animals were allowed to recover for 24 hours prior to administration of drug (GW4064, 100 mg/kg daily in corn oil/10% DMSO) or vehicle alone (in corn oil/10% DMSO) by a daily intra-peritoneal injection for 7 days prior to sacrifice. Animals were allowed food and water ad libitum throughout the study period. Animals were anesthetized with 2–3% isoflurane and sacrificed by cardiac puncture.

Serum levels of alanine aminotransferase (ALT), asparate aminotransferase (AST), total bilirubin (TBILI), and γ-glutamyl transferase (GGT) were determined using an Instrumentation Laboratory Ilab600 clinical chemistry analyzer. Serum bile acids (BILEA) were determined using a commercially available assay (Sigma Chemical Co., St Louis, Mo.).

A section of the liver was removed and placed into 10% neutral buffered formalin. The sections were then perfused and embedded, then sliced and stained, in accordance with well known procedures and examined histologically for necrosis and bile duct proliferation.

What is claimed is:

1. A method of treating cholestasis in a mammalian subject comprising administering to said subject a therapeutically effective amount of an FXR agonist having Formula (II)

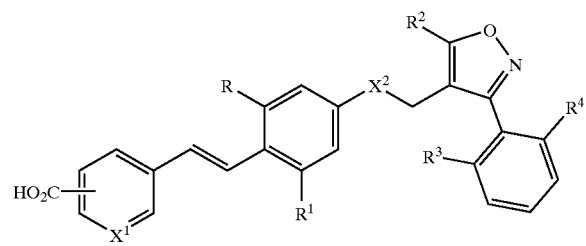

wherein $X^1$ is CH or N; $X^2$ is O or NH; R and $R^1$ are independently H, lower alkyl, halogen, or $CF_3$; $R^2$ is lower alkyl; $R^3$ and $R^4$ are independently H, lower alkyl, halogen, $CF_3$, OH, O-alkyl, or O-polyhaloalkyl.

2. The method of claim 1 wherein the FXR agonist comprises a compound of Formula (I):

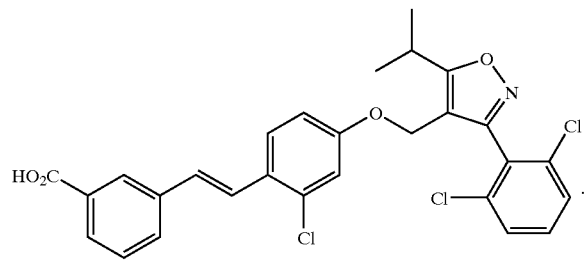

3. A method for treating cholestasis-induced liver damage in a mammalian subject comprising administering to the subject a therapeutically effective amount of a Farnesoid X Receptor (FXR) agonist having Formula (II)

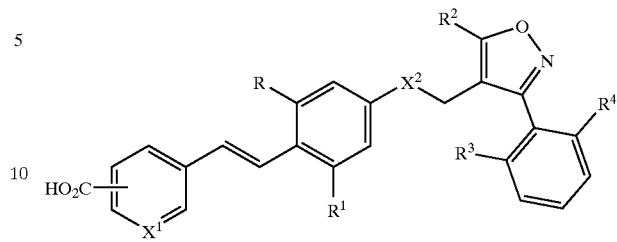

wherein $X^1$ is CH or N; $X^2$ is O or NH; R and $R^1$ are independently H, lower alkyl, halogen, or $CF_3$; $R^2$ is lower alkyl; $R^3$ and $R^4$ are independently H, lower alkyl, halogen, $CF_3$, OH, O-alkyl, or O-polyhaloalkyl.

4. The method of claim 3 wherein the FXR agonist comprises a compound of Formula (I):

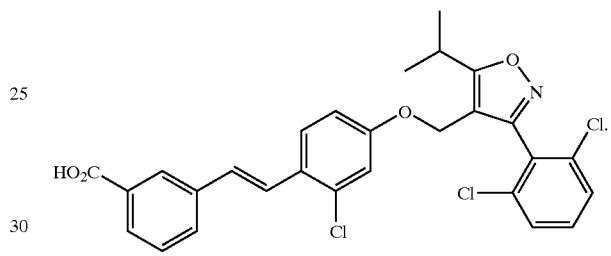

5. A method according to claim 3 where said treatment results in a decrease in a serum marker of liver disease selected from the group consisting of alanine aminotransferase (ALT), asparate aminotransferase (AST), γ-glutamyl transferase (GGT), total serum bilirubin, and serum bile acids.

* * * * *